(12) United States Patent
Kline et al.

(10) Patent No.: US 7,011,835 B1
(45) Date of Patent: Mar. 14, 2006

(54) TARGETED DESTRUCTION OF PESTS

(75) Inventors: Kimberly Kline, Austin, TX (US); Bob G. Sanders, Austin, TX (US)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 09/501,912

(22) Filed: Feb. 10, 2000

Related U.S. Application Data

(63) Continuation of application No. 09/112,874, filed on Jul. 9, 1998, now abandoned.

(60) Provisional application No. 60/052,132, filed on Jul. 10, 1997.

(51) Int. Cl.
*A61K 39/385* (2006.01)

(52) U.S. Cl. .............................. 424/193.1; 530/387.3; 530/391.7

(58) Field of Classification Search .............. 424/183.1; 530/387.3, 391.7
See application file for complete search history.

(56) References Cited

U.S. PATENT DOCUMENTS

| 5,686,600 A | 11/1997 | Carozzi et al. |
| 5,837,242 A | 11/1998 | Holliger et al. |
| 5,870,852 A | 2/1999 | Stanley |

*Primary Examiner*—Patrick J. Nolan
(74) *Attorney, Agent, or Firm*—Benjamin Aaron Adler

(57) ABSTRACT

The present invention is drawn to a safe, cost-effective, environmentally-friendly and ecologically-sound bioengineered pest eradication product and uses thereof. Immunological and genetic engineering techniques are used to generate monoclonal antibodies as well as viruses (phage) that display scFv heavy and/or light chain Ig fragments which exhibit high-avidity specific binding to cells of the microvilli of the midgut of imported fire ant queens. The specific monoclonal antibodies and phage displayed antibody Fab fragments are conjugated to a toxin for targeted delivery and destruction of imported fire ant queens, but not native species.

8 Claims, 4 Drawing Sheets

IMMUNE PRIMING
Immunize mice with imported
fire ant midgut tissue

RNA --> cDNA
Isolate total RNA from spleen of immunized mice,
prepare cDNA by reverse transcription, amplify
by polymerase chain reaction, purify cDNA from gel

**ANTIBODY LIBRARY ON
SURFACE OF PHAGE**
Create phage display library
expressing $10^6$-$10^8$ unique
antibody Fab fragments

DUAL MIDGUT SELECTION
Two-step absorptions to yield
phage displaying antibody fragments
specific for midgut of imported fire ants
and not native fire ants

FINAL MICROVILLI SELECTION
Immunohistochemical verification of
Fab specific to imported fire ant
microvilli cells

TESTING
Test phage/Fab for internalization by
microvilli cells of imported fire ants
when administered by feeding

IMPORTED FIRE ANT ERADICATION
Test phage/Fab/gelonin Conjugate for ability
to selectively kill imported fire ants.

Fig. 1

Figure 2  Evaluation of Monoclonal Antibodies to Midgut Antigens of Imported and Native Fire Ant queens.

Immunohistological analyses of monoclonal antibody binding to the midgut antigens of imported fire ant queens (Positive, B) but not to the midgut antigens of midgut antigens from native fire ants (Native, C). Midgut antigens from imported fire ants reacted with irrelevant antibody did not stain positive and served as the negative control (Control, A)

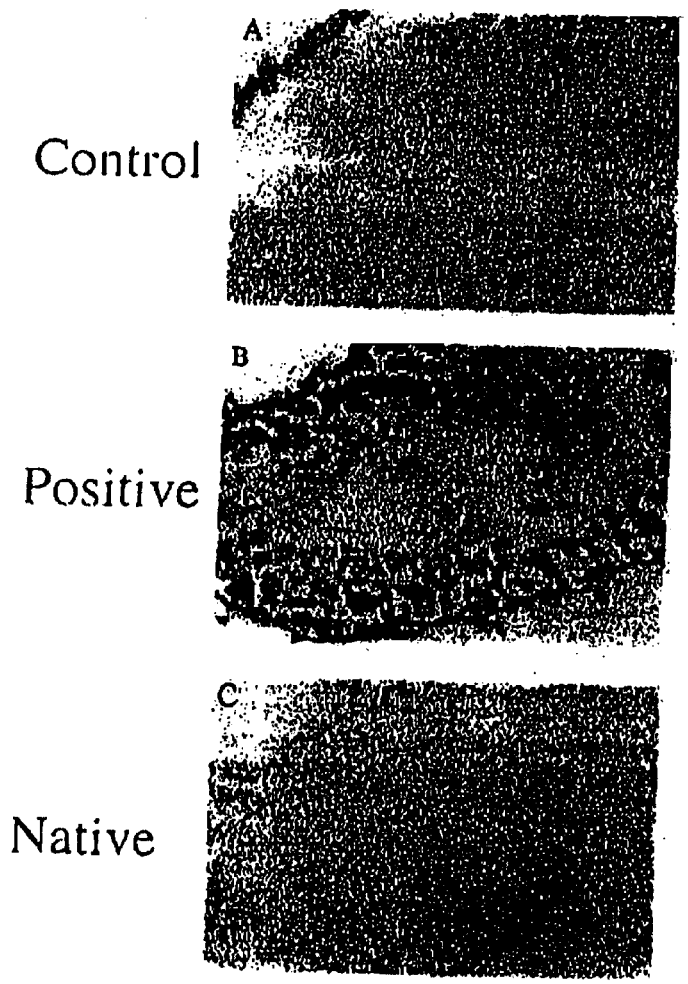

Figure 3 Purification of Phage Displayed Fab to Midgut Antigens of Imported Fire Ant Queens.

EVIDENCE OF PRESENCE OF IG FAB FRAGMENT
C = Control
1-4 = eluted soluble Fab (sFab)
46 = size of Fab fragment (46 Kb)

Western immunoblot analyses show the clone to express Ig Fab. These clones were selected for ability to bind to antigens of the midgut of imported fire ants but not to the midgut antigens of native fire ants.

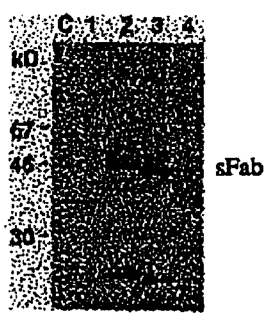

Figure 4. Purification of Phage Displayed Fab to Gelonin

EVIDENCE OF PRESENCE OF IG FAB FRAGMENT FOR TWO CLONES: (pComb3/Fab (6) and pComb3/Fab (47).
IN = Induced
U = Uninduced
V = bacteria containing virus without Ig Fab
46 Kb = size of Fab fragment Western immunoblot analyses show that clones pComb3/Fab (6) and pComb3/Fab (47) express Ig Fab. These clones were selected for ability to bind to gelonin.

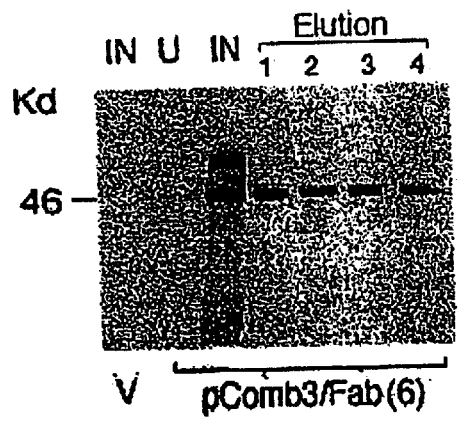

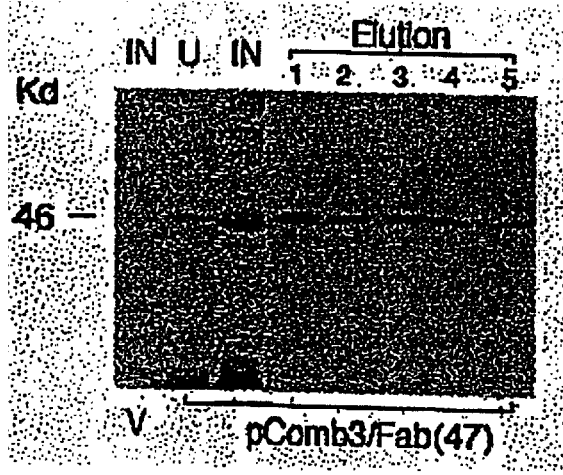

TARGETED DESTRUCTION OF PESTS

CROSS-REFERENCE TO RELATED APPLICATION

This application is a continuation in part of U.S. application Ser. No. 09/112,874, filed Jul. 9, 1998 which claims benefit of provisional application U.S. Serial No. 60/052,132, filed Jul. 10, 1997, now abandoned.

BACKGROUND OF THE INVENTION

1. Field of the Invention

The present invention relates generally to immunology and genetic engineering technology. Specifically, the present invention relates to immunological engineering to produce novel reagents that target poisons to antigens such as cell surface molecules on the cells of microvilli in the midgut of imported fire ant queens and other pests.

2. Description of the Related Art

Imported fire ants are an ecological and financial disaster in Texas as well as other states in the Southern United States. Imported fire ants were accidentally introduced into the U.S. in the 1930s. These pests completely upset and destroy natural ecosystems, and have detrimental economic effects in agriculture (large mounds damage machinery), ranching (loss of newborn livestock), and recreation and tourism (loss of game birds and rendering park and resort areas uncomfortable at best).

A specific problem of fire ant control is how one should control or eliminate imported insect species without destroying native insect species. This problem pertains to numerous non-native animal species that have been introduced in all parts of the United States. Imported species often have a competitive advantage over native species since, in many cases, they have developed enhanced reproductive strategies and do not have natural predators in their new environment (1). Thus, it is important to eliminate the foreign species. On the other hand, the native species should not be eliminated, as the proper balance of a particular ecosystem includes the presence of that native species.

Presently, the art includes the various methods of fire ant control. Chemical poisons, such as AMDRO are well known in the art and are used frequently. Such poisons, however, may pollute the environment, and indiscriminately eliminate native species as well as foreign species.

Thus, the prior art is deficient in an pest eradication product which is environmentally sound and specifically targets and eliminates only pests such as imported fire ants. The present invention fulfills this long-standing need and desire in the art.

SUMMARY OF THE INVENTION

The present invention is drawn to a safe, cost-effective, environmentally-friendly and ecologically-sound bioengineered product for managing pests such as imported fire ants, and a method of making this product. Immunological and genetic engineering echniques are used to generate monoclonal antibodies (mAbs) and resulting Fab fragments as well as viruses (phage) that display antibody fragments, called single heavy or light chain V-gene fragments (scFv) or displayed heavy and light chain V-region fragments (Fab) which exhibit high-avidity specific binding to cells of the pest such as the microvilli of the midgut of imported fire ant queens.

For targeted delivery and destruction of specific pests, but not native species, the specific monoclonal antibodies and phage displayed scFv and Fab fragments are conjugated, e.g., chemically, using established procedures, to toxins such as gelonin, bacterial endotoxins, or other toxins. Furthermore, bispecific Fab's or scFv, with one arm of the Fab exhibiting specificity to the targeted cell membrane extracellular domain, and the other arm of the Fab exhibiting specificity to gelonin, bacterial endotoxin or other toxins provides another novel method for specific targeted delivery of toxins. In yet another method of targeted delivery of toxins, DNA sequences coding regions of the enzymatically active domain of gelonin, bacterial endotoxin or other toxins, or DNA sequences coding for pro-apoptotic inducers, cell cycle blockers, cell proliferation inhibitors, and differentiation inducers can be ligated to DNA coding specific scFv or Fab fragments.

In another aspect of the present invention, there is provided a method for producing reagents that direct poisons to target cells but not to non-target cells, comprising: creating a scFv heavy and/or light chain or Fab Ig fragment-expressing phage display library; selecting said phage display library for antibody fragments that bind to target cells but not to non-target cells; engineering scFv or Fab for non-phage display; amplifying scFv or Fab in *E. coli*; collecting secreted scFv or Fab Ig fragments and attaching said scFv Ig fragments to a toxin.

In yet another aspect of the present invention, there is provided a method of killing a fire ant, comprising the step of contacting said ant with the scFv or Fab polypeptide, such as one produced by the method disclosed herein.

Other and further aspects, features, and advantages of the present invention will be apparent from the following description of the presently preferred embodiments. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. these drawings form a part of the specification. It is to be noted however, that the appended drawings illustrate preferred embodiments of the invention and therefore are not to be considered limiting in their scope.

FIG. 1 depicts schematically the methods of the present invention, including immune priming; cDNA preparation; creation of a phage library; phage selection; verification of specific scFvs and Fabs; and testing thereof.

FIG. 2 shows the immunohistological analyses of monoclonal antibodies binding to midgut antigens of imported and native fire ant queens.

FIG. 2A shows the absence of binding of irrelevant antibody to midgut antigens from imported fire ants and serves as the negative control.

FIG. 2B shows the binding of monoclonal antibody to midgut antigens from imported fire ant queens.

FIG. 2C shows the monoclonal antibody does not bind to midgut antigens from native fire ants.

FIG. 3 shows the purification of phage-displayed Fab's that bind to midgut antigens of imported fire ant queens. Lanes 1–4 show the western blot analysis of clones of Fab Ig selected for binding to midgut antigens of imported fire ants but not to midgut antigens of native fire ants. Lane C is control.

FIG. 4 shows the purification of phage-displayed Fab's that bind to gelonin. Western blot analysis show that clones pComb3/Fab(6) and pComb3/Fab(47) selected for binding to gelonin express the Fab Ig fragments. Lane V shows the bacteria containing virus without Fab Ig. U and IN represent uninduced and induced respectively.

The hybridoma cell lines disclosed herein have been deposited at American Type Culture Collection (10801 University Blvd., Manassas, Va. 20110) on Feb. 3, 2003 and Mar. 27, 2003. The deposited hybridomas are FA1 (patent deposit designation PTA-4703), FA4 (PTA-4704), FA7 (PTA-4705), FA8 (PTA-4706), FA9 (PTA-4707), FA10 (PTA-4708), FA13 (PTA-4709), FA14 (PTA-4710), FA15 (PTA-4711), FA17 (PTA-4712), G1 (PTA-4713), G2 (PTA-4714), G3 (PTA-4715), G4 (PTA-4716), G5 (PTA-4717), G6 (PTA-4718), and G7 (PTA-4719). In compliance with 37 C.F.R. §1.808(a), the deposit was made under the conditions that all restrictions imposed by the depositor on the availability of the deposited material to the public will be irrevocably removed upon the granting of the patent.

DETAILED DESCRIPTION OF THE INVENTION

The present invention is directed to a pest eradication product comprising: a peptide directed against an antigenic epitope of a gastrointestinal or digestive tract target cell of said pest; and a toxin. This product will have utility against a wide variety of pests, including imported fire ant queens, roaches, termites, mosquitoes, rodents, and birds. Representative toxins which may be used in this product include gelonin, bacterial endotoxin, ribosome inactivating proteins, pro-apoptotic agents, cell cycle blockers, cell proliferation inhibitors, and cell differentiation inhibitors. Preferably, the target cell is a cell in the microvilli of the midgut region of an imported fire ant. In one embodiment, the peptide is an antibody or antibody fragment specific to said antigen. Representative examples of a peptide directed against said target cell antigen is an antibody secreted from hybridoma selected from the group consisting of FA1, FA4, FA7, FA8, FA9, FA10, FA13, FA14, FA15, and FA17.

The present invention is also directed to a pest eradication product comprising: a peptide directed against an antigenic epitope of a gastrointestinal or digestive tract target cell of said pest; a peptide directed against an antigenic epitope of a toxin; and a toxin. This product will have utility against a wide variety of pests, including imported fire ant queens, roaches, termites, mosquitoes, rodents, and birds. Representative toxins which may be used in this product include gelonin, bacterial endotoxin, ribosome inactivating proteins, pro-apoptotic agents, cell cycle blockers, cell proliferation inhibitors, and cell differentiation inhibitors. Preferably, the target cell is a cell in the microvilli of the midgut region of an imported fire ant. In one embodiment, the peptide is an antibody or antibody fragment specific to said antigen. Representative examples of a peptide directed against said target cell antigen is an antibody secreted from hybridoma selected from the group consisting of FA1, FA4, FA7, FA8, FA9, FA10, FA13, FA14, FA15, and FA17. Representative examples of a peptide directed against said toxin is an antibody secreted from hybridoma selected from the group consisting of G1, G2, G3, G4, G5, G6, and G7. Preferably, the peptide directed against said toxin is an antibody fragment derived from phage display library clone selected from the group consisting of pComb3/Fab(6) and pComb3/Fab(47).

The present invention is also directed to a method of killing a pest, comprising the step of contacting said pest with a pest eradication product disclosed herein.

The present invention is also directed to a peptide directed against a target cell antigen, wherein said peptide is an antibody secreted from hybridoma selected from the group consisting of FA1, FA4, FA7, FA8, FA9, FA10, FA13, FA14, FA15, and FA17.

In another embodiment of the present invention, there is provided a peptide directed against a toxin, wherein said peptide is an antibody secreted from hybridoma selected from the group consisting of G1, G2, G3, G4, G5, G6, and G7.

The present invention is also directed to a peptide directed against a toxin, wherein said peptide is an antibody fragment derived from phage display library clone selected from the group consisting of pComb3/Fab(6) and pComb3/Fab(47).

The following definitions are given for the purpose of facilitating understanding of the inventions disclosed herein. Any terms not specifically defined should be interpreted according to the common meaning of the term in the art.

As used herein, the term "monoclonal antibody" or "mAb" refers to an antibody comprised of immunoglobulin heavy and light polypeptide chains with specificity to target cells and is generated and selected from a cloned antibody producing cell.

As used herein, the term "antibody fragment" or "Fab" refers to immunoglobulin based recognition units of minimum size comprised of V-gene segments from immunoglobulin heavy and light chains that exhibit high affinity to target antigens.

As used herein, the "scFv" fragment refers to immunoglobulin based recognition unit of minimum size, a single heavy or light chain, or combined heavy and light chain V-gene 1 g fragment (referred to as Fab) with high affinity to target cell.

As used herein, the term "bispecific antibody" refers to either chemically derived or DNA technology derived Fab or scFv immunoglobulin fragments with specificity to two different antigenic determinants, i.e., one arm of the Ig specificity unit reacting with targeted antigen and the other arm reacting specifically with toxins such as gelonin or bacterial endotoxins.

As used herein, the term "phage display library" refers to repertoire of up to $2 \times 10^8$ independent clones of immunoglobulin Fab or scFv fragments. Phage displaying fab were screened and selected for specificity to midgut antigenic epitopes of imported fire ant queens.

As used herein the term "toxin" refers to any chemical that behaves in a toxic manner in that it kills cells when introducted into target cells, by being delivered by distinct mechanisms: chemically linked to targeted Ig fragment, bispecific Fab technology, or by DNA technology providing scFv heavy chain-toxin cytotoxic domain. A representative toxin is gelonin, a well-known ribosome inactivating protein or recombinant forms thereof. As used herein, the term "toxin" refers to any chemicals that are "pro-apoptotic", "cell cycle blockers", "cell proliferation inhibitors" and "cell proliferation agents", e.g., cDNA from genes that control cell proliferation, cell cycle, cell differentiation, and cell death.

As used herein, the term "phage displayed Fab" and "phage displayed scFv" refers to a repertoire of Fab or scFv heavy and/or light chain Ig fragments that are displayed on phage and selected through specificity binding to antigenic epitopes of target cells.

In accordance with the present invention there may be employed conventional molecular biology, immunology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" (R. I. Freshney, ed. (1986)); "Immobilized Cells And Enzymes" (IRL Press, (1986)); B. Perbal, "A Practical Guide To Molecular Cloning" (1984).

A "vector" is a replicon, such as a plasmid, phage or cosmid, to which another DNA segment may be attached so as to bring about the replication of the attached segment. A vector is said to be "pharmacologically acceptable" if its administration can be tolerated by a recipient mammal. Such an agent is said to be administered in a "therapeutically effective amount" if the amount administered is physiologically significant. An agent is physiologically significant if its presence results in a change in the physiology of a recipient mammal. For example, in the treatment of retroviral infection, a compound which decreases the extent of infection or of physiologic damage due to infection, would be considered therapeutically effective.

A cell has been "transformed" by exogenous or heterologous DNA when such DNA has been introduced inside the cell. The transforming DNA may or may not be integrated (covalently linked) into the genome of the cell. In prokaryotes, yeast, and mammalian cells, for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Transcriptional and translational control sequences are DNA regulatory sequences, such as promoters, enhancers, polyadenylation signals, terminators, and the like, that provide for the expression of a coding sequence in a host cell.

A "DNA molecule" refers to the polymeric form of deoxyribonucleotides (adenine, guanine, thymine, or cytosine) in either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

Production and screening of monoclonal antibodies with high avidity to specific antigenic epitopes is a well-established and standard laboratory procedure. DNA technology well known to those having ordinary skill in this art permits the introduction of DNA coding for small immunoglobulin recognition units (called antibody fragments i.e., N-terminal variable domains of heavy and light immunoglobulin chains that exhibit the same antigenic specificity as the intact larger parent antibody) into virus expression vectors (phage) that produce and display the scFv heavy and light chains and combinations of heavy and light chain Ig fragments on their surface (2–9). This technology has been used to specifically target tumor cells for selected destruction; however, to date, this technology has not been applied to specifically target insect pests or other animal pests for destruction.

The phage display method represents a major advance over traditional monoclonal antibodies in that large and diverse repertoires of scFv heavy or light and combinations of heavy and light chain Ig V-region genes can be generated and expressed on the surface of viruses; thereby permitting rapid screening and selection for high-avidity (tight binding) scFv Ig fragments with targeted specificity. Importantly, once specific phage-displayed scFv Ig fragments have been selected for specificity to an antigenic epitope, the DNA that codes for the specific Fab fragment is available for genetic engineering with DNA coding for enzymatically active domain of gelonin, bacterial endotoxins, or other toxins, programmed cell death (apoptotic) genes as well as genes that disrupt cell proliferation. Producing scFv or Fab Ig fragments with targeted specificity and possess enzymatically active gelonin or bacterial endotoxins or other cell death inducing gene products provides a novel method for targeted delivery of cell death inducing products.

The present invention is directed to a pest eradication product comprising a peptide directed against a gastrointestinal or digestive tract target cell antigen of said pest; and a toxin. In one aspect of this pest eradication product, the peptide is an antibody specific for midgut antigenic epitopes of imported fire ant queens. The target cell antigen, however, may be any antigen in the gastrointestinal or digestive tract of the pest. A representative gastrointestinal or digestive tract antigen is found in the microvilli of the midgut region of an imported fire ant. However, the target specificity is not limited to the mircovilli or imported fire ants, but encompass any cell, tissue or organ of any animal species in which the destruction of such cells or tissues or organs results in the containment or elimination of the animal species. In addition to specifically targeting imported fire ant queens for destruction, this technology has applications in the selected destruction of all other insect pests such as termites, mosquitoes, and roaches as well as pests of different genera including reptiles, avians and mammals. The pest eradication product may contain various toxins. Representative toxins that disrupt cellular transcription and translation include ribosome inactivating proteins, pro-apoptotic agents, cell cycle blockers, cell proliferation inhibitors, and cell differentiation inhibitors.

In one embodiment of the present invention, there is provided a method of killing an imported fire ant, comprising the step of contacting said ant with a fire ant eradication product comprising: a peptide directed against a gastrointestinal or digestive tract target cell antigen of the fire ant; and a toxin. Preferably, the said peptide is an antibody specific to the antigen and the target cell is a cell in the microvilli of the midgut region of an imported fire ant queens. Another method for targeted delivery of toxin involves phage displayed libraries of peptides or proteins that are selected for specificity to midgut antigenic epitopes of imported fire ant queens. Many different toxins can be utilized with the targeted delivery systems. As examples, the toxin may be selected from the group consisting of a ribosome inactivating protein, a pro-apoptotic agent, a cell cycle blockers, a cell proliferation inhibitor or cell differentiation inhibitors.

The following examples are given for the purpose of illustrating various embodiments of the invention and are not meant to limit the present invention in any fashion:

EXAMPLE 1

Production, Screening and Testing of Hybridomas to Imported Fire Ant Midgut Antigens Hybridoma production Imported fire ants were collected from ant mounds at the University of Texas Brackenridge Field Laboratory, Austin, Tex. Midguts were taken from approximately 100 imported fire ant queens, and minced in phosphate buffered saline. Three BALB/c mice received multiple subcutaneous and intraperitoneal immunizations with midgut immunogen preparations from imported fire ant queens. At the completion of the immunizations, spleens were removed. Spleens were cut into two equal sections, one to be used for preparation of hybridomas and the other section to be used for phage displayed Fab fragments. For hybridomas, spleen cells were harvested and fused to the SP2/0-Ag14 myeloma cell line (purchased from ATCC). Following fusion, cells were cultured and selected for hybridomas following standard monoclonal antibody production procedures.

Hybridoma screening Hybridomas were cloned by limiting dilution. Hybridoma supernatants were first screened for the presence of mouse immunoglobulins (IgG or IgM) by ELISA, using rabbit antibodies specific for murine IgG or IgM. Ig-secreting hybridomas identified by ELISA were then tested for the ability of cell supernatants to bind to 5 micron cross sections of imported fire ant midguts as determined by immunohistochemical staining. Hybridomas were next screened for ability to specifically react with micron cryocut cross sections of midgut from imported fire ant queens but not to 5 micron midgut sections from native fire ant queens, using immunohistological analyses. For these studies, frozen cross sections of midguts from imported fire ant queens and native fire ant queens were air dried and fixed with ice cold acetone. The sections were blocked with normal rabbit serum and then incubated with hybridoma supernatants at room temperature for 30 minutes, and washed three times. Next, the sections were reacted with biotinylated rabbit anti-mouse Ig (rabbit antibodies that detected both murine IgG and IgM immunoglobulins) (VECTASTAIN Elite ABC Kit, Vector Laboratories) for 30 minutes, followed by three washes. The sections were then reacted with VECTASTAIN Elite ABC Reagent and developed with DAB(Vector Labs) using the nickel enhancement. Supernatants from hybridomas of interest were isotyped as to immunoglobulin class and light chain type by ELISA. Hybridomas of interest were frozen and stored in liquid nitrogen for future use, whereas supernatants were stored at minus 70° C. for future analysis and affinity purification.

Characterization of hybridomas Analyses of supernatants from 18 hybridomas by immunohistological analyses revealed 11 monoclonals that were positive for the midgut antigens of imported fire ant queens and negative to the mid gut antigens of native fire ant queens, 2 monoclonals that were negative for midgut antigens from both imported and native fire ant queens, and 5 monoclonals that were positive for midgut antigens from both imported and native fire ant queens (Table 1). Isotyping of the Ig's revealed all monoclonals to express kappa light chain type, 12 expressed IgM, 3 expressed IgG1, 1 expressed IgG3, and 2 expressed IgG2a. Of the 11 monoclonals that were positive for midgut antigens of imported fire ant queens and negative for midgut antigens of native fire ant queens, 8 were IgM, 2 were IgG1, and 1 was IgG2a. typical data of immunohistological analyses of midgut tissue sections are depicted in FIG. 2, showing a positive reaction with midgut tissue from an imported fire ant queen (FIG. 2B), a negative reaction with midgut tissue from a native fire ant queen (FIG. 2C), and a negative reaction with midgut tissue section from imported fire ant queen treated with irrelevant antibody (FIG. 2A).

TABLE 1

Characterization of Hybridoma Clones

| Clone Sections Number | Clone Designation | Ig Titer (ELISA) | Ig Isotype (H and L) | Reaction with Midgut Imported | Native |
|---|---|---|---|---|---|
| FA1 | 1G747C5F7G10 | M | IgM, K | Positive | Negative |
| FA2 | 1F11E305C11C10 | H | IgM, K | Positive | Positive |
| FA3 | 2A5G5A1B1B2 | M | IgM, K | Positive | Positive |
| FA4 | 2A7A2F7C10F8 | M | IgM, K | Positive | Negative |
| FA5 | 2E10D10E9F2F1 | L | IgG1, K | Positive | Positive |
| FA6 | 2F11FSH4D9G9 | L | IgG3, K | Positive | Positive |
| FA7 | 2H2D11D2F2D2 | M | IgG1, K | Positive | Negative |
| FA8 | 2H6C5B8E4Fs | M | IgM, K | Positive | Negative |
| FA9 | 4A7E6D6D5H5 | M | IgM, K | Positive | Negative |
| FA10 | 4B11H12G1OD7E10 | M | IgM, K | Positive | Negative |
| FA11 | 4E7C6C12F10G11 | M | IgG2a, K | Negative | Negative |
| FA12 | 4G5A9A1H11F11 | M | IgM, K | Positive | Positive |
| FA13 | 5A1E3D12B5D1 | M | IgG2a, K | Positive | Negative |
| FA14 | 5A7H9C3E1G2 | H | IgM, K | Positive | Negative |
| FA15 | 5B6B1D4F3F4 | H | IgM, K | Positive | Negative |
| FA16 | 6ABF6C10D11B12 | M | IgM, K | Negative | Negative |
| FA17 | 6B384FD4B12 | L | IgG1, K | Positive | Negative |
| FA18 | 6E7C7B10E7C5 | M | IgM, K | Negative | Negative |

Elisa assay (Ig titre) was used to screen supernatants for expression of immunoglobulins (H, M, and L refer to high, moderate, and low levels of Ig) prior to screening by immunohistological analyses for ability to react with the midgut antigens of imported and native fire ants. Data is recorded as positive or negative (negative reactions included no detectable reaction to an extremely low level of reaction). Mouse isotype as to heavy and light chain was determined.

Affinity purification of IgG and IgM Cultures of hybridomas which had been stored in liquid nitrogen were established in standard hybridoma medium. After the cultures were well established the cultures were weaned onto Protein Free Hybridoma Medium (PFHM—Life Technologies, Gaithersburg, Md.), to eliminate serum in the culture. Cells for production of antibody were allowed to overgrow for 3 days at which time the supernatant (growth media) was collected, quick frozen in a dry ice/ethanol bath and stored at −70° C. for subsequent purification. To purify, supernatants were thawed and concentrated using a Centricon 3 (MWCO 3000) at 4° C. The concentrated samples were then purified using either an Immunopure (A/G) IgG Purification Kit or an Immunopure IgM Purification Kit (Pierce, Rockford, Ill.) following the protocols included with the kit. The selected antibodies were then desalted. IgG's were desalted using the columns that were included with the (A/G) IgG kit, and the IgM's were desalted using D-salt Dextran Desalting columns (Pierce). Once purified the IgG's were aliquoted and stored at −20° C. and the IgM's were brought to 50% glycerol and stored at −20° C.

EXAMPLE 2

Production, Screening, and Testing of Phage Displayed Ig Fragments to Midgut Antigens of Imported Fire Ants cDNA synthesis RNA was isolated from mouse spleens (½ spleen from mice immunized with midgut preparations from 9 imported fire ant queens as described in Example 1)

using the guanidium isothiocyanate method. cDNA was prepared from 5 micrograms of RNA with oligo (dT)$_{16}$ as a primer. Reverse transcriptase, nucleotides, and buffers were purchased from PERKIN ELMER (RNA PCR Kit, Branchburg, N.J.) and were used according to the instructions provided by the manufacturer. Fd and L chain cDNA were amplified by PCR. The 5' primers used were Light chain (GTGCCAGATGTGAGCTCGTGATGACCCAGTCTCCA, SEQ ID NO:1), V heavy chain a (AGGTCCAGCTGCTCGAGTCTGG, SEQ ID NO:2), VHb (AGGTCCAGCTGCTCGAGTCAGG, SEQ ID NO:3), V heavy chain c (AGGTCCAGCTTCTCGAGTCTGG, SEQ ID NO:4), and V heavy chain D (AGGTCCAGCTTCTCGAGTCAGG, SEQ ID NO:5) which introduced restriction sites (Sac I for light chains and XHO 1 for heavy chains) that facilitate their directional cloning into pComb 3. The 3' primers used were k chain (TCCTTCTAGATTACTAACACTCTCCCCTGTTGAA, SEQ ID NO:6), C heavy 1 (AGGCTTACTAGTACAATCCCTGGGCACAAT, SEQ ID NO:7), thereby the k chain primer introduced an Xba 1 site and the heavy chain primer introduced a Spe 1 site. General conditions for PCR were Taq polymerase (Perkin Elmer, Branchburg, N.J.) at 2.5 U/100-microliter reaction mixtures, 200 micromolar deoxynucleoside triphosphates, 1 millimolar MgCl$_2$, 5 microliters of cDNA per 100 microliters of reaction mixture, 150 ng of 5' primer and 150 ng of 3' primer in 1× buffer as supplied by the manufacturer (Perkin Elmer). Reaction mixtures were cycled at 94° C. for 1.5 minutes, 52° C. for 2.5 minutes, and 72° C. for 3 minutes for a total of 40 cycles. These conditions have generated products of the correct size (660 bp) on all samples.

Phage display library construction The M13 phage surface display vector pComb3 was provided by The Scripps Research Institute, LaJolla, Calif. The pComb3 vector and light chain PCR fragments were digested with Sac I and Xba I (Boehringer Mannheim, Indianapolis, Ind.) for three hours. The restricted DNA were purified by electroelution from agarose gels after electrophoresis. Vector and light chain inserts were ligated at approximately 1:3 molar ratio with T4 DNA ligase (Stratagene, LaJolla, Calif.) overnight at 4° C. After ligation, 300 microliters of E. coli XL1-Blue was transformed by electroporation with 5 microliters of ligation mixture. The light chain library was propagated in bulk as an overnight culture in super broth medium (SB; 30 g of tryptone, 20 g of yeast extract, 10 grams of MOPS per liter, pH 7.0) supplemented with tetracycline at 10 micrograms/ml and carbenicillin at 50 micrograms/ml. Phagemid DNA which contained light chain inserts was isolated and digested with XhoI and Spe1 and gel purified. Fd PCR fragments were digested and purified in the same manner, and ligated into the restricted plasmid to produce a combinatorial library containing both Fd and L chain genes. After transformation, 3 mls of SOC medium (Molecular Cloning, Cold Spring Harbor Laboratory Press, 1989) was added, and the culture was shaken at 220 rpm for 1 hour at 37° C., after which 10 mls of SP medium containing tetracycline at 10 micrograms/ml and carbenicillin at 20 micrograms/ml was added; the culture was then shaken at 300 rpm for an additional hour. After this culture period carbenicillin was added to a final concentration of 50 micrograms/ml and incubation continued for another hour.

The cells were coinfected with the replication-deficient helper phage BCSM13 ($10^{12}$ PFU) in 100 ml of SB medium containing micrograms/ml of tetracycline and 50 micrograms/ml of carbenicillin, and the culture was shaken for 2 hours. After this time, kanamycin at 70 micrograms/ml was added, and the culture was incubated at 37° C. overnight. Phage were isolated from culture supernatants by 4% (wt/vol) polyethylene glycol 8000 and 3% (wt/vol) NaCl precipitation. Phage pellets were resuspended in TBS (50 mM Tris-HCl, pH 7.5/150 millimolar NaCl) plus 1% BSA.

Selection of phages One hundred imported fire ant queen midguts were homogenized and resuspended in TBS plus 1% BSA and incubated for 20 minutes with rotation. Then 0.5 mls of the above phage/Fab preparation were added and incubated for another 2 hours. After washing 10 times with TBST (0.5% Tween 20), the bound phage were eluted with 0.1 molar HCl (pH 2.2) mg/ml of BSA at room temperature and immediately neutralized with 2 molar Tris base. The eluted phage were infected with 2 ml of fresh XL1-Blue (O.D600=1) at room temperature for 15 minutes, then 10 mls of pre warmed SB medium containing tetracycline at 10 micrograms/ml and carbenicillin at 20 micrograms/ml was added; phage preparation, and panning were repeated as described above.

Phage displaying Ig fragments that were selected for ability to react with midgut antigens from imported fire ant queens underwent further panning, utilizing midgut preparations from native fire ant queens in order to enrich phage with specificity to midgut antigens of imported fire ant queens. Phage preparations were permitted to react with homogenized midgut antigen preparations from native fire ants, and supernatant containing phage that failed to react with midgut antigens of native fire ants were collected for further study after the homogenates were pelleted by centrifugation.

Testing of phage transit in live imported fire ant queens Colonies of imported fire ants were established so that each colony had at least 5 or more queens (each colony was set up from a single mound collection). After establishment of the colonies, soluble M13 Phage were placed in glucose water (10% glucose w/v) and the ants were allowed to consume the glucose phage mixture ad libutum. Fire ant queens were collected 24, 48 and 72 hours after the phage solution was introduced. Midguts were isolated and homogenized in PBS, then centrifuged to remove any debris. The resulting mixture was plated at various dilutions in LB top agar containing 40 ul of a solution of X-gal (20 mg/ml in dimethylformamide) and 4 ul of IPTG (200 mg/ml) which was poured onto LB plates. The plates were covered and the top agar was allowed to harden. The plates were then inverted and incubated at 37° C. Colonies were present at 12 and 24 hours following plating. Pale blue plaques began to form in as little as 4 hours and fully developed by 8–12 hours. Incubation at 4° C. for a few hours helps intensify the color. These data show that phage displaying Fab fragments can be successfully introduced to the midguts of live imported fire ant queens via feeding.

Purification of soluble Ig fragments from phage display library To prepare Fab in soluble form, pComb3 phagemid DNA containing L chain and Fd genes was restricted with Spe I and NHe 1 to remove the M13 gene coding sequence. The digested plasmid (4.7 kb) was self-ligated and transferred to XL1-Blue bacteria cells. Individual bacteria colonies were grown for 6 hours at 37° C., then induced with 1 mM IPTG overnight at 30° C. with shaking.

Bacteria were harvested by centrifugation and soluble Fab was extracted from the periplasmic space by freezing in a d ry ice-ethanol bath for 5 minutes followed by thawing in 37° C. water bath (this process was repeated 4 times). The soluble Fab (46 Kd at non-reduced condition) was analyzed by Western Blot as shown in FIG. 3. The specific antibody was also analyzed by Immunohistochemical staining using a rabbit antimouse IgG Fab antibody (Cotex Biochemicals) as the primary antibody.

EXAMPLE 3
Production Screening and Testing of hybridomas to gelonin
Hybridoma Production Gelonin was purchased from Sigma (St. Louis, Mo.). Gelonin was solubilized in Phosphate Buffered Saline (PBS) at 200 mg/ml, and then mixed with an equal volume of complete Freund's adjuvant to form an emulsion. Balb/C mice (6 weeks of age or older) received 0.5 ml of above immunogen by an intraperitoneal injection. Three weeks after the intraperitoneal injection the mice were subcutaneously injected with 50 mg of gelonin in PBS only, and this subcutaneous injection was repeated twice over a two weeks time period. At the completion of the immunizations (three days after the last subcutaneous injection), spleens were removed. Spleens were cut into two equal sections, one to be used for preparation of hybridomas and the other section to be used for production of phage displaying Fab fragments. For hybridomas, spleen cells were harvested and fused to the SP2/0-Ag14 myeloma cell line (purchased from ATCC). Following fusion, cells were cultured and selected for hybridomas following standard monoclonal antibody production procedures.

Hybridoma screening Hybridomas were cloned by limiting dilution. Hybridoma supernatants were screened for ability to react with gelonin, using an ELISA assay. Supernatants from hybridomas of interest were isotyped as to immunoglobulin class and light chain type by ELISA. Hybridomas of interest were frozen and stored in liquid nitrogen for future use, whereas supernatants were stored at minus 70° C. for future analysis and affinity purification.

Characterization of hybridomas Isotope analyses of supernatants from 7 hybridomas with strong reactivity to gelonin by ELISA revealed that all monoclonals with specificity to gelonin were of the IgG1 class and kappa light chain type (Table 2).

TABLE 2

Isotype Characterization of Supernatants from Hybridomas Secreting Antibodies Specific to Gelonin

| Clone # Type | Original Clone | Mouse Ig Class | Light Chain |
| --- | --- | --- | --- |
| G1 | 1F2E11E3C2D8 | IgG1 | Kappa |
| G2 | 2C10B2F6B9C6 | IgG1 | Kappa |
| G3 | 2C12F12E4B8C2 | IgG1 | Kappa |
| G4 | 2C12G9A4B6B8 | IgG1 | Kappa |
| G5 | 2E1D9E11F3F3 | IgG1 | Kappa |
| G6 | 3G8D3C10D8D7 | IgG1 | Kappa |
| G7 | 4G12B8D7B10D3 | IgG1 | Kappa |

Affinity purification of IgC Affinity purification IgG1 from hybridomas secreting antibodies specific for gelonin was performed as described in Example 1.

EXAMPLE 4
Production screening, and testing of phage displayed Ig fragments to gelonin cDNA synthesis RNA was isolated from mouse spleens (½ of spleen from mice immunized with gelonin as described in Example 3) using the guanidium isothiocyanate method. cDNA synthesis and PCR were carried out as described in Example 2.

Phage display library construction Phage display library was constructed as described in Example 2.

Selection of phages Phage bearing Fab fragments on their surface were selected by panning on gelonin coated wells. Wells of a microtiter plate were coated overnight at 4° C. with 1 mg of gelonin solubilized in PBS (phosphate buffered saline). The wells were washed three times with TBST (0.5% Tween 20), then blocked with TBS plus 3% BSA (bovine serum albumin) at 37° C. for 1 hour. Bocking solution was removed, and 50 ul of above phage preparations were added and incubated for an additional 2 hours at 37° C. After washing ten times with TBST, the phage that bound to gelonin were eluted with 0.1 Molar HCl (pH 2.2)/1 mg/ml of BSA at room temperature and immediately neutralized with 2 M Tris base. The eluted phage were mixed with 2 mls of fresh XL1-blue bacteria ($O.D._{600}=1$) at room temperature for 15 minutes, then added to 10 mls of pre-warmed SB medium containing tertracycline at 10 mg/ml and carbenicillin at 20 ug/ml and permitted to grow. For enrichment purposes, the phage preparation and panning were repeated as described above.

Purification of soluble Ig fragments from phage display library Fab in soluble form was prepared as described in Example 2. The soluble Fab (46 Kd at non-reduced condition) was analyzed by Western Blot, and specificity to gelonin was analyzed by ELISA. Western immunoblot analyses of soluble Fab from two different preparations are depicted in FIGS. 4A and B.

EXAMPLE 5
Targeted Delivery of Toxin to Midgut of Imported Fire Ant Queens
The above selected and purified monoclonal antibodies and phage displayed Fab's to midgut antigens of imported fire ants and to the toxin gelonin were used to specifically deliver gelonin to the midgut of imported fire ant queens. The toxin gelonin serves as the prototype for the targeted delivery of toxins; however, the monoclonal antibodies and phage displayed Fab fragments with specificity to midgut antigens of imported fire ant queens can be used for specific delivery of other toxic agents to the midgut of imported fire ants.

Established technologies (10–12) were used for gelonin attachment to Ig, Fab, and $Fab_2$ for the specific delivery of gelonin to the midgut of imported fire ant queens. Before forming Ig/gelonin complexes, tests were performed to determine if monoclonal antibodies, Fab, and $Fab_2$ fragments with specificity to midgut antigens possess the ability to kill imported fire ant queens in the absence of toxin. Gelonin can be conjugated via a stable thioether linkage to purified monoclonal antibodies, to purified Fab fragments generated by papain or pepsin digestion, or to scFv fragments generated from phage display library. Fab fragments with specificity to the midgut antigens of imported fire ants can also be conjugated via a stable thioether linkage to antibody fragments with specificity to gelonin to generate bispecific antibodies. Furthermore, polypeptides that bind specifically to midgut antigens of imported fire ant queens and contain an enzymatically active domain of a toxin can be generated by DNA technology and genetic engineering technologies (13, 14).

The following references were cited herein:
1. Rolldobler, B. and E. O. Wilson 1990. The Ants. The Belknap Press, Cambridge, Mass.
2. Barbas, C. and R. Lerner. 1991. Combinatorial immunoglobulin libraries on the surface of phage (phabs): rapid selection of antigen-specific. Fab. Methods: Comp. Met. Enzym.2: 119.
3. Ames, R., M. Tornetta, C. Jones and P. Tsui. 1994. Isolation of neutralizing anti-C5a antibodies from a filamentous phage monovalent Fab display library. J. Immun. 152:4572.

4. Ames, et al (15 co-authors). 1995. Neutralizing murine monoclonal antibodies to human IL-5 isolated from hybridomas and a filamentous phage Fab display library. J. Immunol. 154:6355.
5. Winter, G., A. D. Griffiths, R. E. Hawkins and H. R. Hoogenboom. 1994. Making antibodies by phage display technology. Ann. Rev. Immunol. 12:433.
6. Vaughan, T. J., et al., 0.1996. Human antibodies with sub-nanomolar affinities isolated from a large non-immunized phage display library. Nature Biotech. 14: 309.
7. Kruif, J. de, et al., 1996. New perspectives on recombinant human antibodies. Immunology Today 17:453.
8. Kruif, J. de, and T. Logtenberg. 1996. Leucine zipper dimerized bivalent and bispecific scFv antibodies from a semi-synthetic antibody phage display library. J. Bio. Chem. 271:7630.
9. Davies, J. and L. Riechmann. 1995. Antibody VH domains as small recognition units. Biotechnology 13:475.
10. French, R, C. Penney, A. Browning, F. Stirpe, A. George and M. Glennie. 1995. Delivery of the ribosome-inactivating protein, gelonin, to lymphoma cells via CD22 and CD38 using bispecific antibodies. Brit. J. Cancer 71:986.
11. Better, M., S. Bernhard, D. Fishwild, P. Nolan, R. Bauer, A. Kung, and S. Carroll. 1994. Gelonin analogs with engineered cysteine residues form antibody immunoconjugates with unique properties. J. Biol. Chem. 269:9644.
12. Glennie, M. J., H. M. McBride, A. T. Worth, and G. T. Stevenson. Preparation and performance of bispecific $F(ab'\_)_2$ antibody containing thioether-linked Fab'_ fragments. J. Immunol. 139:2367–2375, 1987.
13. Holliger, P., and G. Winter. Engineering bispecific antibodies. Current Opinion in Biotechnology 4: 446–449, 1993.
14. Maurer-Gebhard, M., M. Schmidt, M. Azemar, U. Altenschmidt, E Stocklin, W. Wels, and B. Groner. Systemic treatment with a recombinant erbB-2 receptor-specific tumor toxin efficiently reduces pulmonary metastases in mice injected with genetically modified carcinoma cells. Cancer Res. 58:2661–2666, 1998.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A pest eradication product comprising an antibody or an antibody fragment directed against the microvilli in the midgut region of an imported fire ant queen, wherein said antibody or antibody fragment is fused to a toxin, wherein said antibody is secreted from a hybridoma selected from the group consisting of FA1 (PTA-4703), FA4 (PTA-4704), FA7 (PTA-4705), FA8 (PTA-4706), FA9 (PTA-4707), FA10 (PTA-4708), FA13 (PTA-4709), FA14 (PTA-4710), FA15 (PTA-4711), and FA17 (PTA-4712).

2. The pest eradication product of claim 1, wherein said toxin is selected from the group consisting of gelonin, bacterial endotoxin, ribosome inactivating proteins, pro-apoptotic agents, cell cycle blockers, cell proliferation inhibitors, and cell differentiation inhibitors.

3. A pest eradication product comprising a first antibody or fragment thereof directed against the microvilli in the midgut region of an imported fire ant queen, wherein said first antibody or fragment thereof is fused to a second antibody or fragment thereof directed against an antigenic epitope of a toxin, and a toxin, wherein said first antibody is secreted from a hybridoma selected from the group consisting of FA1 (PTA-4703), FA4 (PTA-4704), FA7 (PTA-4705), FA8 (PTA-4706), FA9 (PTA-4707), FA10 (PTA-4708), FA13 (PTA-4709), FA14 (PTA-4710), FA15 (PTA-4711), and FA17 (PTA-4712), said second antibody is secreted from a hybridoma selected from the group consisting of G1 (PTA-4713), G2 (PTA-4714), G3 (PTA-4715), G4 (PTA-4716), G5 (PTA-4717), G6 (PTA-4718), and G7 (PTA-4719).

4. The pest eradication product of claim 3, wherein said toxin is selected from the group consisting of gelonin, bacterial endotoxin, ribosome inactivating proteins, pro-apoptotic agents, cell cycle blockers, cell proliferation inhibitors, and cell differentiation inhibitors.

5. A method of killing an imported fire ant queen, comprising the step of contacting said fire ant queen with the pest eradication product of claim 1.

6. A method of killing an imported fire ant queen, comprising the step of contacting said fire ant queen with the pest eradication product of claim 3.

7. A peptide directed against a target cell antigen, wherein said peptide is an antibody secreted from hybridoma selected from the group consisting of FA1 (PTA-4703), FA4 (PTA-4704), FA7 (PTA-4705), FA8 (PTA-4706), FA9 (PTA-4707), FA10 (PTA-4708), FA13 (PTA-4709), FA14 (PTA-4710), FA15 (PTA-4711), and FA17 (PTA-4712).

8. A peptide directed against a toxin, wherein said peptide is an antibody secreted from hybridoma selected from the group consisting of G1 (PTA-4713), G2 (PTA-4714), G3 (PTA-4715), G4 (PTA-4716), G5 (PTA-4717), G6 (PTA-4718), and G7 (PTA-4719).

* * * * *

SEQUENCE LISTING

```
<160> NUMBER OF SEQ ID NOS: 7

<210> SEQ ID NO 1
<211> LENGTH: 35
<212> TYPE: DNA
<213> ORGANISM: Artificial Sequence
<220> FEATURE:
<221> NAME/KEY: primer_bind
<223> OTHER INFORMATION: 5' light chain primer

<400> SEQUENCE: 1
gtgccagatg tgagctcgtg atgacccagt ctcca                              35

<210> SEQ ID NO 2
<211> LENGTH: 22
<212> TYPE: DNA
<213> ORGANISM: Artificial Sequence
<220> FEATURE:
<221> NAME/KEY: primer_bind
<223> OTHER INFORMATION: 5' V heavy chain A primer

<400> SEQUENCE: 2
aggtccagct gctcgagtct gg                                            22

<210> SEQ ID NO 3
<211> LENGTH: 22
<212> TYPE: DNA
<213> ORGANISM: Artificial Sequence
<220> FEATURE:
<221> NAME/KEY: primer_bind
<223> OTHER INFORMATION: 5' Vhb primer
```

-continued

```
<400> SEQUENCE: 3
aggtccagct gctcgagtca gg                                              22

<210> SEQ ID NO 4
<211> LENGTH: 22
<212> TYPE: DNA
<213> ORGANISM: Artificial Sequence
<220> FEATURE:
<221> NAME/KEY: primer_bind
<223> OTHER INFORMATION: 5' V heavy chain c primer

<400> SEQUENCE: 4
aggtccagct tctcgagtct gg                                              22

<210> SEQ ID NO 5
<211> LENGTH: 22
<212> TYPE: DNA
<213> ORGANISM: Artificial Sequence
<220> FEATURE:
<221> NAME/KEY: primer_bind
<223> OTHER INFORMATION: 5' V heavy chain D primer

<400> SEQUENCE: 5
aggtccagct tctcgagtca gg                                              22

<210> SEQ ID NO 6
<211> LENGTH: 34
<212> TYPE: DNA
<213> ORGANISM: Artificial Sequence
<220> FEATURE:
<221> NAME/KEY: primer_bind
<223> OTHER INFORMATION: 3' k chain primer

<400> SEQUENCE: 6
tccttctaga ttactaacac tctcccctgt tgaa                                 34

<210> SEQ ID NO 7
<211> LENGTH: 30
<212> TYPE: DNA
<213> ORGANISM: Artificial Sequence
<220> FEATURE:
<221> NAME/KEY: primer_bind
<223> OTHER INFORMATION: 3' C heavy 1 primer

<400> SEQUENCE: 7
aggcttacta gtacaatccc tgggcacaat                                      30
```